United States Patent
Wang et al.

(10) Patent No.: US 9,980,791 B1
(45) Date of Patent: May 29, 2018

(54) ORTHODONTIC REMODELING DEVICE

(71) Applicant: METAL INDUSTRIES RESEARCH & DEVELOPMENT CENTRE, Kaohsiung (TW)

(72) Inventors: Yue-Jun Wang, Kaohsiung (TW);
Tung-Lin Tsai, Kaohsiung (TW);
Chun-Chieh Tseng, Kaohsiung (TW);
Li-Wen Weng, Kaohsiung (TW);
Chih-Lung Lin, Kaohsiung (TW)

(73) Assignee: Metal Industries Research & Development Centre, Kaohsiung (TW)

( * ) Notice: Subject to any disclaimer, the term of this patent is extended or adjusted under 35 U.S.C. 154(b) by 0 days. days.

(21) Appl. No.: 15/490,957

(22) Filed: Apr. 19, 2017

(30) Foreign Application Priority Data

Feb. 8, 2017 (TW) .............................. 106104156 A (51) Int. Cl.
*A61C 7/10* (2006.01)
*A61C 7/18* (2006.01)

(52) U.S. Cl.
CPC . *A61C 7/10* (2013.01); *A61C 7/18* (2013.01)

(58) Field of Classification Search
CPC .................................... A61C 7/10; A61C 7/18
USPC ................................................. 433/7, 18, 19
See application file for complete search history.

(56) References Cited

U.S. PATENT DOCUMENTS

| | | | | |
|---|---|---|---|---|
| 4,144,643 A * | 3/1979 | Krygier | .................... | A61C 7/10 433/7 |
| 4,571,178 A * | 2/1986 | Rosenberg | ................ | A61C 7/10 433/18 |
| 5,564,920 A * | 10/1996 | Klapper | .................... | A61C 7/10 433/7 |
| 5,885,290 A * | 3/1999 | Guerrero | .............. | A61B 17/663 433/7 |
| 6,267,589 B1 * | 7/2001 | Farzin-Nia | ................ | A61C 7/10 433/7 |
| 6,302,687 B1 * | 10/2001 | King | .................... | A61B 17/663 433/18 |
| 6,520,772 B2 | 2/2003 | Williams | | |
| 7,588,579 B2 * | 9/2009 | Mommaerts | ......... | A61B 17/663 606/105 |

(Continued)

FOREIGN PATENT DOCUMENTS

TW            531409 B        5/2003

*Primary Examiner* — Nicholas Lucchesi
(74) *Attorney, Agent, or Firm* — Alan D. Kamrath; Kamrath IP Lawfirm, P.A.

(57) ABSTRACT

An orthodontic remodeling device includes a sleeve having first and second screw holes in two ends thereof. The first and second screw holes have opposite thread directions. A first screw rod includes a first threaded portion threadedly engaged with the first screw hole and a first assembling portion exposed outside of the sleeve. A second screw hole includes a second threaded portion threadedly engaged with the second screw hole and a second assembling portion exposed outside of the sleeve. Two tooth pushing members are respectively engaged with the first and second assembling portions. Each tooth pushing member includes at least one tooth coupling ring mounted on at least one tooth of a patient for pushing the at least one tooth outward. The sleeve is rotatable to move the first and second screw rods toward or away from each other to change a relative position between the two tooth pushing members.

7 Claims, 7 Drawing Sheets

(56) References Cited

U.S. PATENT DOCUMENTS

| | | | | |
|---|---|---|---|---|
| 2002/0031741 A1* | 3/2002 | Williams | .................. | A61C 7/10 |
| | | | | 433/19 |
| 2003/0194675 A1* | 10/2003 | Williams | .................. | A61C 7/10 |
| | | | | 433/18 |
| 2005/0203534 A1* | 9/2005 | Mommaerts | ......... | A61B 17/663 |
| | | | | 606/90 |
| 2010/0151402 A1* | 6/2010 | Williams | .................. | A61C 7/00 |
| | | | | 433/7 |
| 2013/0252195 A1* | 9/2013 | Popat | ....................... | A61C 7/10 |
| | | | | 433/24 |
| 2016/0120622 A1* | 5/2016 | Montalban | ............... | A61C 7/10 |
| | | | | 433/7 |

* cited by examiner

ORTHODONTIC REMODELING DEVICE

CROSS REFERENCE TO RELATED APPLICATIONS

The application claims the benefit of Taiwan application serial No. 106104156, filed on Feb. 8, 2017, and the entire contents of which are incorporated herein by reference.

BACKGROUND OF THE INVENTION

1. Field of the Invention

The present invention relates to an orthodontic remodeling device and, more particularly, to an orthodontic remodeling device to be mounted in a mouth of a patient for pushing teeth outward.

2. Description of the Related Art

Current orthodontic devices generally include a dental brace used with arch wires for correcting teeth irregularities. However, the arch wires can only provide forces to pull teeth and, thus, provide a limited and slow correction effect on irregular teeth located inward of the regular dentition line.

SUMMARY OF THE INVENTION

To solve the above problem, the present invention provides an orthodontic remodeling device that can be mounted in a mouth of a patient to push indented teeth outward, and arch wires can be used subsequently to apply forces for correcting and positioning the teeth.

When the terms "up", "top", "down", "bottom", "left", "right", "inner", "outer", "side", and similar terms are used herein, it should be understood that these terms have reference only to the structure shown in the drawings as it would appear to a person viewing the drawings and are utilized only to facilitate describing the embodiments of the invention, rather than restricting the invention.

An orthodontic remodeling device according to the present invention includes a sleeve having a first screw hole in an end thereof and a second screw hole in another end thereof. The first screw hole has a thread direction opposite to a thread direction of the second screw hole. A first screw rod includes a first threaded portion and a first assembling portion. The first threaded portion is threadedly engaged with the first screw hole. The first assembling portion is exposed outside of the sleeve. A second screw rod includes a second threaded portion and a second assembling portion. The second threaded portion is threadedly engaged with the second screw hole. The second assembling portion is exposed outside of the sleeve. Two tooth pushing members are respectively engaged with the first and second assembling portions. Each of the two tooth pushing members includes at least one tooth coupling ring adapted to be mounted on at least one tooth of a patient and adapted to push the at least one tooth outward. The sleeve is rotatable to move the first and second screw rods toward or away from each other to change a relative position between the two tooth pushing members.

Thus, the orthodontic remodeling device according to the present invention can be mounted in a mouth of a patient to push indented teeth outward, and arch wires can be used subsequently to apply pushing forces for correcting and positioning the teeth, thereby increasing the effect and efficiency of correcting irregular teeth.

In an example, the first screw hole has a central axis coincident to a central axis of the second screw hole.

In an example, the first screw hole and the second screw hole have an identical pitch, such that the first and second screw rods move at the same speed through the same distance.

In an example, the sleeve includes an intermediate portion having hexagonal cross sections. Such a structure is easy to process and reduces slipping while rotating the sleeve.

In an example, the at least one tooth coupling ring of each of the two tooth pushing members is a closed, annular ring having an inner periphery corresponding to a contour of the to-be-pushed-outward tooth. This structure permits the inner periphery of the tooth coupling ring to fittingly abut an outer periphery of the tooth to be pushed outward, providing uniform outward pushing of the tooth.

In an example, one of the two tooth pushing members includes a tooth coupling ring rotatably connected to the first assembling portion, and the other of the two tooth pushing members includes a tooth coupling ring rotatably connected to the second assembling portion. Thus, each tooth coupling ring can be rotated to a desired angular position according to the orientation of the tooth of the patient, improving the operational smoothness of mounting around the tooth of the patient.

In an example, each of the two tooth pushing members includes a plurality of tooth coupling rings, and two adjacent tooth coupling rings is connected by a connecting plate. The first assembling portion is rotatably connected to one of the connecting plate and the plurality of tooth coupling rings of one of the two tooth coupling members. The second assembling portion is rotatably connected to one of the connecting plate and the plurality of tooth coupling rings of the other of the two tooth coupling members. Thus, each tooth coupling ring can be rotated to a desired angular position according to the orientation of the tooth of the patient, improving the operational smoothness of mounting around the tooth of the patient.

In an example, the one of the connecting plate and the plurality of tooth coupling rings, which is rotatably connected to the first assembling portion, is located at a middle portion of the one of the two tooth pushing members. Furthermore, the one of the connecting plate and the plurality of tooth coupling rings, which is rotatably connected to the second assembling portion, is located at a middle portion of the other of the two tooth pushing members.

In an example, the first screw rod has first and second axial ends. The first assembling portion is disposed on the first axial end of the first screw rod. The first screw rod has a maximum diameter from the first axial end through the second axial end of the first screw rod. The second screw rod has first and second axial ends. The second assembling portion is disposed on the first axial end of the second screw rod. The second screw rod includes a receiving hole having an opening in the second axial end of the second screw rod. The receiving hole has a minimum diameter larger than the maximum diameter of the first screw rod. The first threaded portion is movable into the receiving hole when the sleeve is rotated to move the first and second screw rods toward each other. Thus, the relative displacement of the first and second screw rods toward or away from each other can be increased.

In an example, the first and second screw rods have an identical configuration except the thread directions to increase the manufacturing convenience.

In an example, the first screw rod has first and second axial ends. The first assembling portion is disposed at the first axial end of the first screw rod. The first screw rod further includes a first stopper portion on the second axial end thereof. The first stopper portion has a planar end face. The first threaded portion is located between the first assembling portion and the first stopper portion. The second screw rod has first and second axial ends. The second assembling portion is disposed on the first axial end of the second screw rod. The second screw rod further includes a second stopper portion on the second axial end of the second screw rod. The second stopper portion has a planar end face. The second threaded portion is located between the second assembling portion and the second stopper portion. The sleeve is rotatable to move the first and second screw rods toward each other until the first and second stopper portions of the first and second screw rods abut each other. Thus, the first and second screw rods approaching each other can stably abut each other to avoid deformation and misalignment of the first and second screw rods.

The present invention will become clearer in light of the following detailed description of illustrative embodiments of this invention described in connection with the drawings.

DETAILED DESCRIPTION OF THE INVENTION

Figure 1:
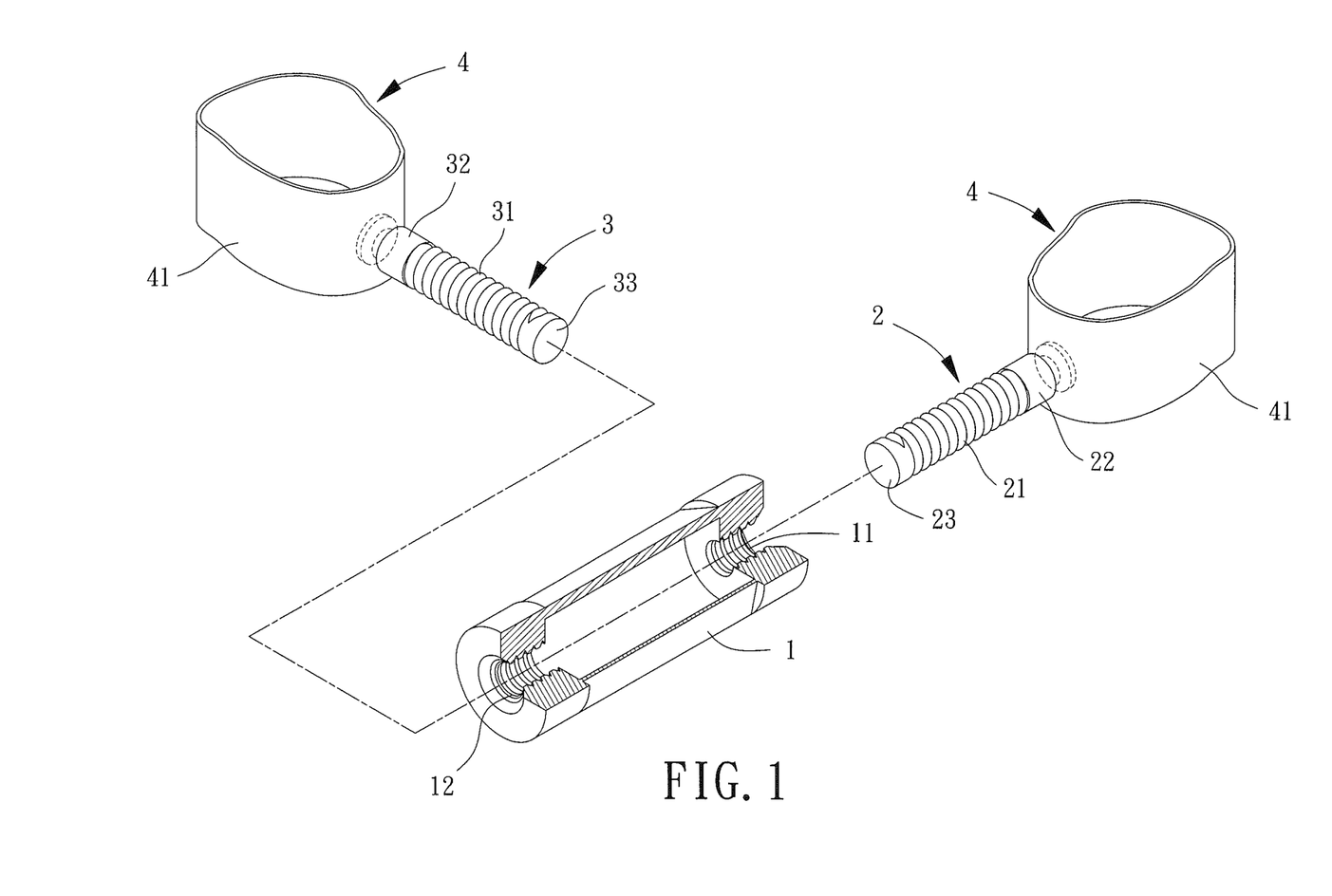
FIG. 1 is an exploded, perspective view of an orthodontic remodeling device of a first embodiment according to the present invention.
Figure 2:
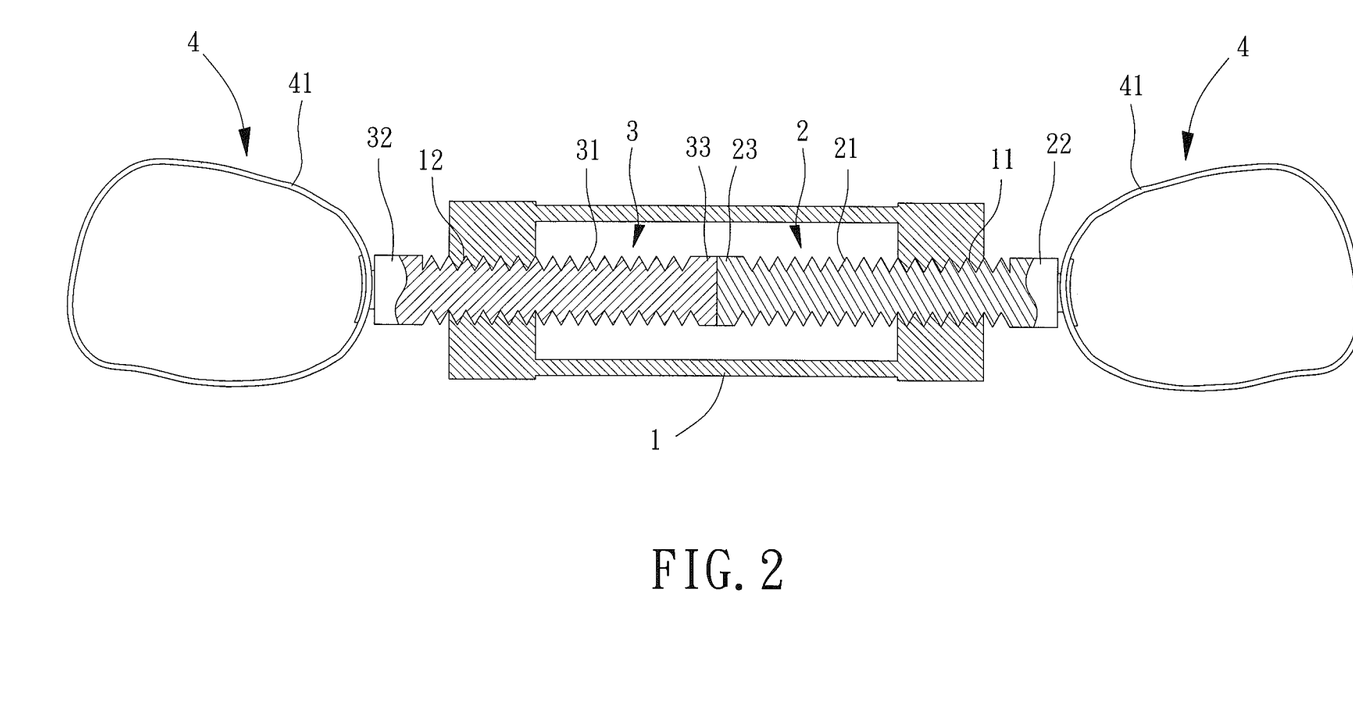
FIG. 2 is a cross sectional view of the orthodontic remodeling device of FIG. 1 after assembly.

With reference to FIGS. 1 and 2, an orthodontic remodeling device of a first embodiment according to the present invention can be made of pure titanium or titanium alloy (such as Ti-6A-14V alloy, TiNi alloy, or Ti15Mo alloy), medical grade stainless steel (such as 304 stainless steel, 316 stainless steel, or 410 stainless steel), or medical grade Co—Cr—Mo alloy. Furthermore, the orthodontic remodeling device can be produced by at least one of 3D printing, CNC processing, casting, or wire cutting. The orthodontic remodeling device includes a sleeve 1, a first screw rod 2, a second screw rod 3, and two tooth pushing members 4. The first and second screw rods 2 and 3 are threadedly engaged with the sleeve 1. The two tooth pushing members 4 are exposed outside of the sleeve 1 and respectively engage with the first and second screw rods 2 and 3.

The sleeve 1 has a hollow interior and includes two ends aligned in an axial direction. A first screw hole 11 is formed in one of the two ends of the sleeve 1 for threading connection with the first screw rod 2. A second screw hole 12 is formed in the other end of the sleeve 1 for threading connection with the second screw rod 3. The sleeve 1 can be rotated to synchronously move the first and second screw rods 2 and 3 toward or away from each other. The sleeve 1 is not restricted in the outline. As an example, the sleeve 1 can have a non-smooth cylindrical outline to reduce slipping while rotating the sleeve 1. As a non-restrictive example, an intermediate portion of the sleeve 1 can have hexagonal cross sections that are easy to process.

Note that the thread direction of the first screw hole 11 is opposite to the thread direction of the second screw hole 12. For example, the second screw hole 12 has a right-handed inner thread when the first screw hole 11 has a left-handed inner thread. In another example, the second screw hole 12 has a left-handed inner thread when the first screw hole 11 has a right-handed inner thread. Preferably, the first screw hole 11 has a central axis coincident to a central axis of the second screw hole 12. The first screw hole 11 and the second screw hole 12 can have an identical pitch, such that the first and second screw rods 2 and 3 move at the same speed through the same distance.

Despite the opposite thread directions, the outlines of the first and second screw rods 2 and 3 can be identical or different according to needs. In this embodiment, the first and second screw rods 2 and 3 have an identical configuration except the thread directions, such that it is not necessary to sort the first and second screw rods 2 and 3 before forming the threads. This allows rapid mass production of the semi-products of the first and second screw rods 2 and 3, increasing the manufacturing convenience.

Specifically, the first screw rod 2 includes a first threaded portion 21 and a first assembling portion 22. The first threaded portion 21 is threadedly engaged with the first screw hole 11, and the first assembling portion 22 is exposed outside of the sleeve 1 for connection with one of the tooth pushing members 4. In this embodiment, the first assembling portion 22 is disposed at a first axial end of the first screw rod 2. A first stopper portion 23 is formed on a second axial end of the first screw rod 2. The first stopper portion 23 can have a planar end face. The first threaded portion 21 is located between the first assembling portion 22 and the first stopper portion 23.

Likewise, the second screw rod 3 includes a second threaded portion 31 and a second assembling portion 32. The second threaded portion 31 is threadedly engaged with the second screw hole 12, and the second assembling portion 32 is exposed outside of the sleeve 1 for connection with the other tooth pushing member 4. In this embodiment, the second assembling portion 32 is disposed at a first axial end of the second screw rod 3. A second stopper portion 33 is formed on a second axial end of the second screw rod 3. The second stopper portion 33 can have a planar end face. The second threaded portion 31 is located between the second assembling portion 32 and the second stopper portion 33.

When the sleeve 1 is rotated in a direction, the first and second screw rods 2 and 3 synchronously move toward each other. When the first and second screw rods 2 and 3 are closest to each other (see FIG. 2), the first stopper portion 23 of the first screw rod 2 stably abuts the second stopper portion 33 of the second screw rod 3, such that an operator can feel the abutting and then stop rotating the sleeve 1, avoiding deformation and misalignment of the first and second screw rods 2 and 3. On the other hand, when the sleeve 1 is rotated in the reverse direction, the first and second screw rods 2 and 3 synchronously move away from each other, such that the two tooth pushing members 4 exert outward forces on two teeth of a patient to which the two tooth pushing members 4 are mounted, thereby pushing the two teeth outward.

Figure 3:
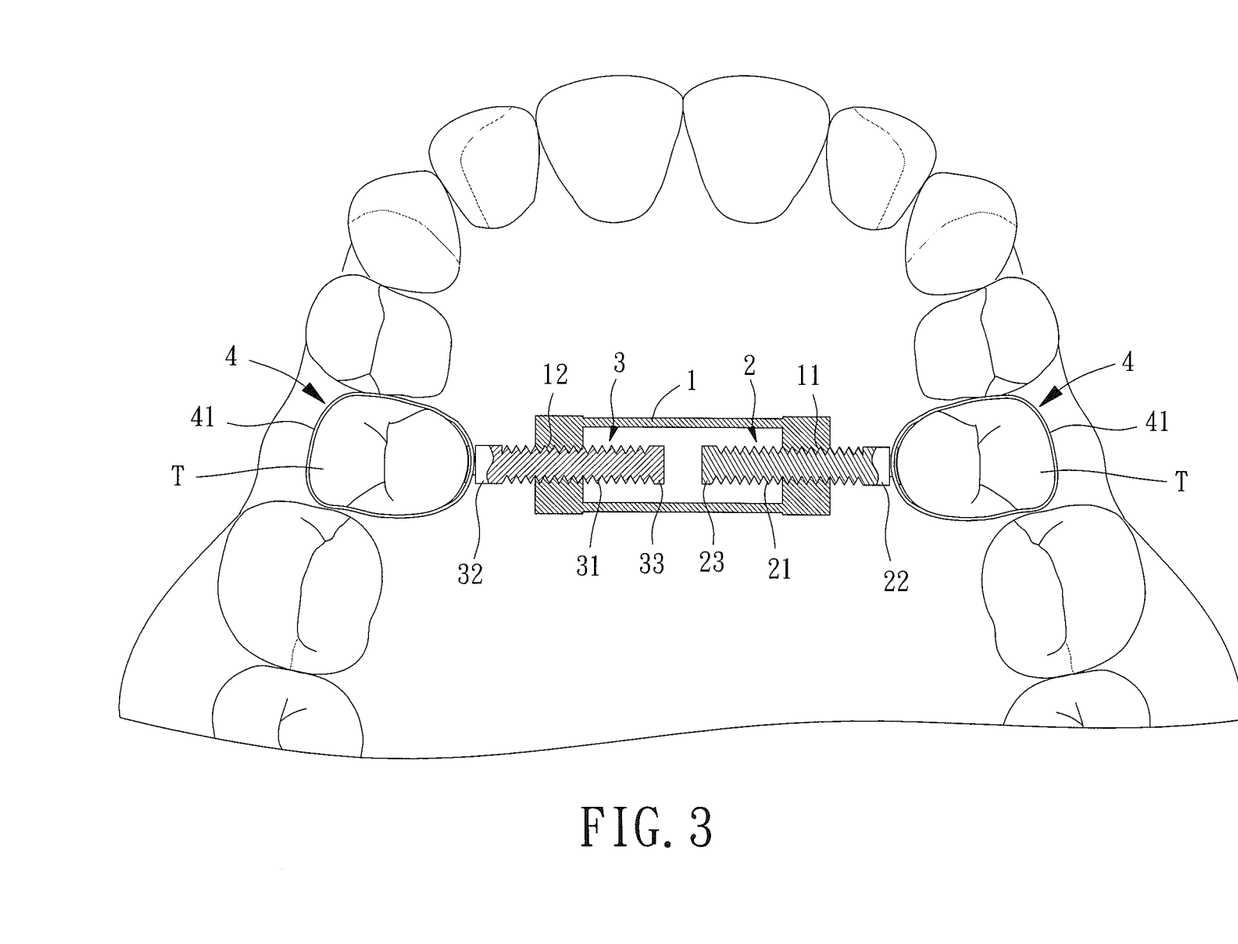
FIG. 3 is a diagrammatic view illustrating use of the orthodontic remodeling device of FIG. 2 on two indented teeth of a patient.

With reference to FIGS. 1 and 3, each tooth pushing member 4 includes a tooth coupling ring 41 adapted to be mounted on a to-be-pushed-outward tooth in a mouth of a patient. The tooth coupling rings 41 are respectively and rotatably engaged with the first assembling portion 22 of the first screw rod 2 and the second assembling portion 32 of the second screw rod 3. Each tooth coupling ring 41 can be C-shaped to provide an opening permitting elastic deformation of the tooth coupling ring 41 for easy mounting on a tooth of the patient and for easy removal of the tooth coupling ring 41 from the tooth of the patient. Alternatively, as shown in the figures, each tooth coupling rings 41 can be custom-made to include an inner periphery corresponding to the contour of the tooth T to be pushed outward. Furthermore, each tooth coupling ring 41 can be a closed, annular ring to maintain the outline, such that the inner periphery of the tooth coupling ring 41 fittingly abuts an outer periphery of the tooth T to be pushed outward. This provides uniform outward pushing of the to-be-pushed-outward tooth T, avoiding concentration of the pushing force on a local area of the tooth T which damages the tooth T and causes pain to the patient.

Furthermore, in this embodiment, the second axial end of the first assembling portion 22 of the first screw rod 2 extends through an annular wall of one of the tooth coupling rings 41 and is riveted from the inside of the corresponding tooth coupling ring 41. Thus, the corresponding tooth coupling ring 41 can be rotated relative to the first screw rod 2 to a desired angular position according to the orientation of the tooth T of the patient for smoothly mounting around the tooth T of the patient. The other tooth coupling ring 41 can be rotatably connected to the second assembling portion 32 of the second screw rod 3 by the same structure.

With reference to FIG. 3, according to the above structure, when the orthodontic remodeling device according to the present invention is used to correct irregular teeth of a patient, the operator places the orthodontic remodeling device into a mouth of the patient and rotates the sleeve 1 to adjust the two tooth pushing members 4 to have a suitable spacing therebetween. Next, the two tooth pushing members 4 are mounted around two to-be-pushed-outward teeth T respectively on left and right sides of the upper jaw of the patient, rapidly completing mounting of the orthodontic remodeling device. After mounting, the operator slightly rotates the sleeve 1 to slightly and synchronously move the first and second screw rods 2 and 3 away from each other, such that the two tooth pushing members 4 exert outward pushing forces on the two to-be-pushed-outward teeth T coupled with the two tooth pushing members 4.

Figure 4:
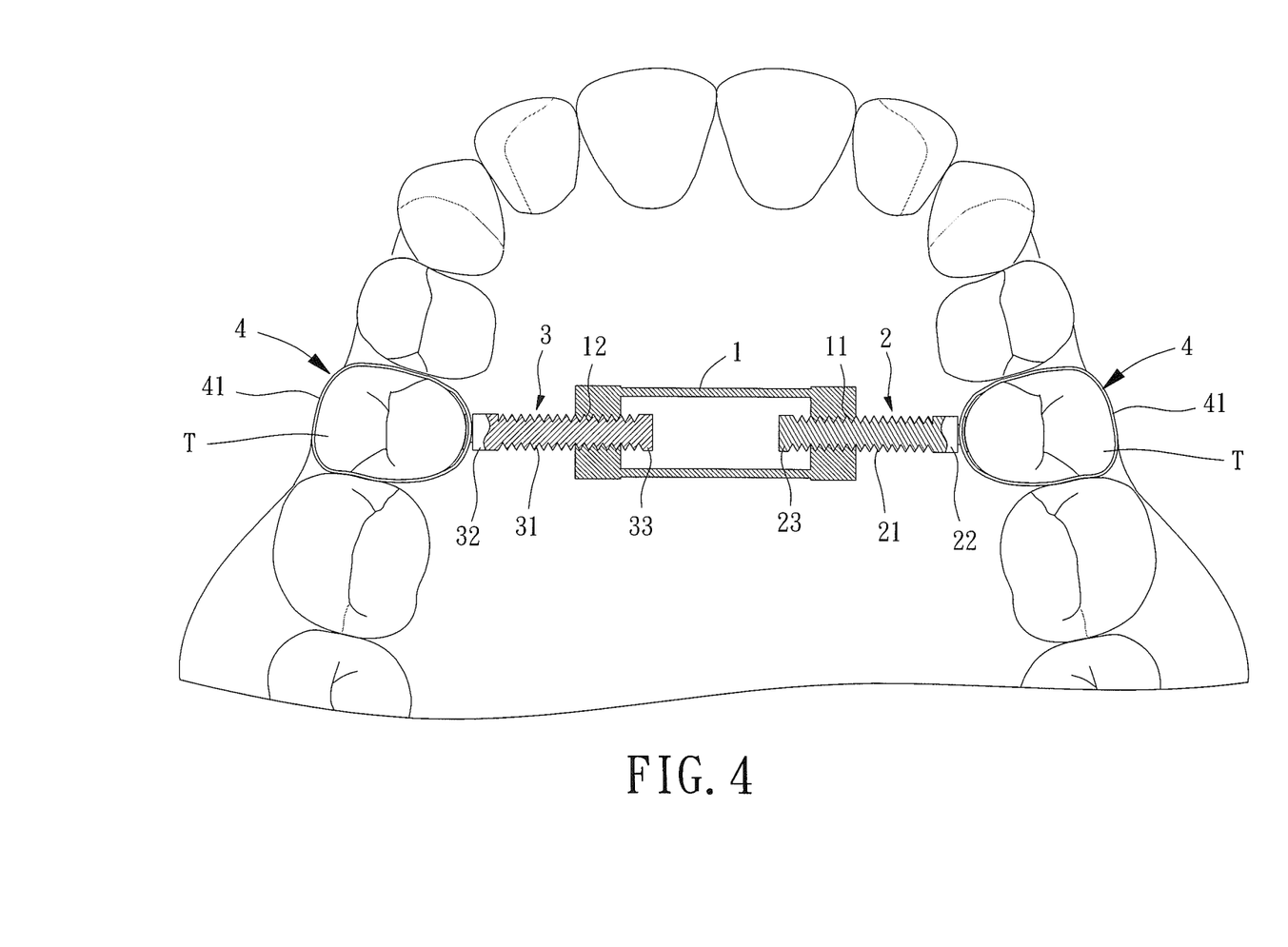
FIG. 4 is a diagrammatic view similar to FIG. 3, with the two indented teeth pushed outward.

With reference to FIG. 4, since the two to-be-pushed-outward teeth T can be pushed to gradually move outward, the sleeve 1 can be rotated periodically to gradually push the two to-be-pushed-outward teeth T outward until the two to-be-pushed-outward teeth T are pushed back to the normal dentition line or even slightly protrude outward of the normal dentition line. Next, the orthodontic remodeling device can be removed, and arch wires can be used to apply pulling forces to correct and position each tooth, accomplishing correction of the irregular teeth.

Figure 5:
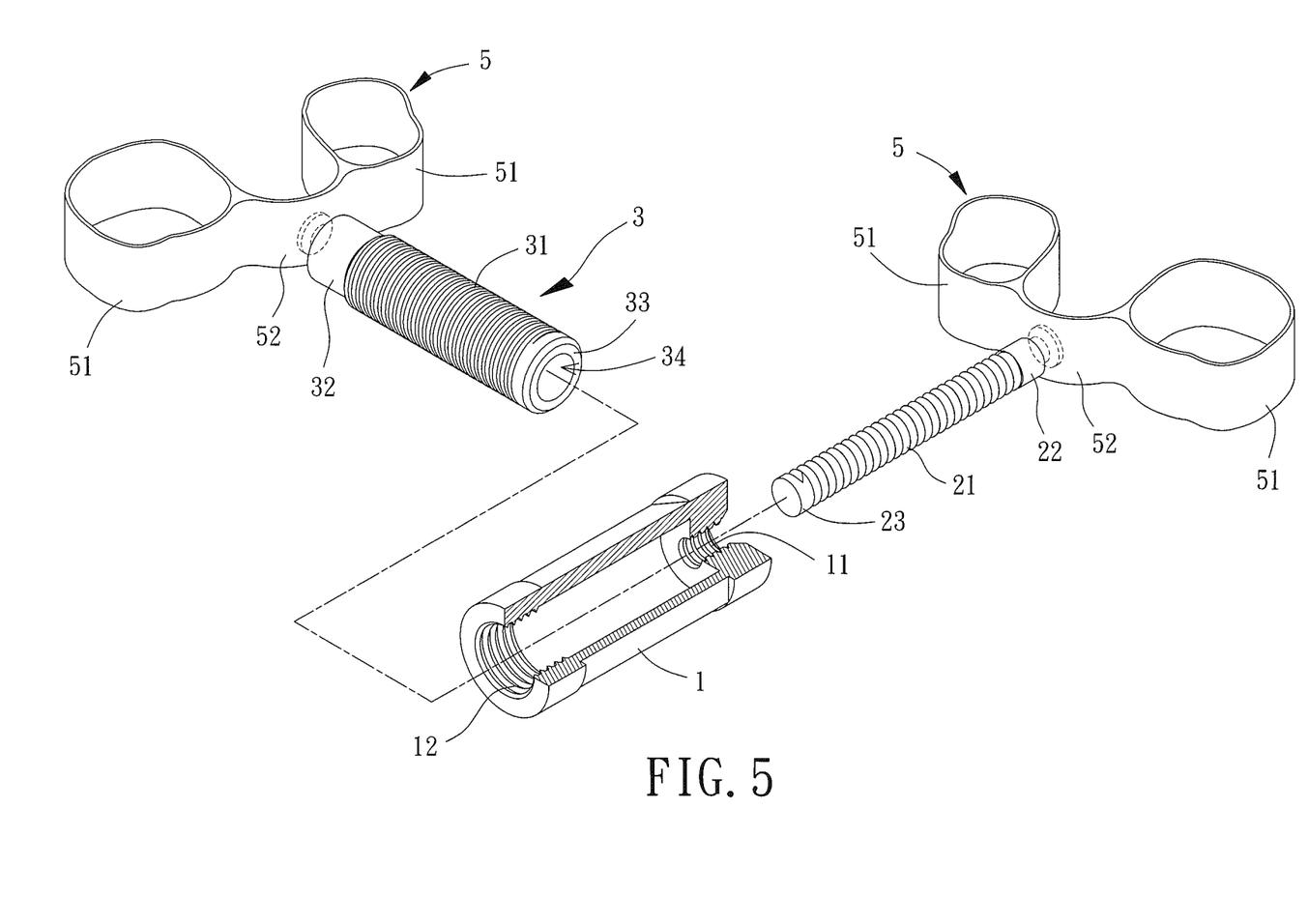
FIG. 5 is an exploded, perspective view of an orthodontic remodeling device of a second embodiment according to the present invention.

FIG. 5 shows an orthodontic remodeling device of a second embodiment according to the present invention which is substantially the same as the first embodiment. The main differences are that, in the second embodiment, one of the first and second screw rods 2 and 3 is a tube having a larger diameter, and the other is a rod having a smaller diameter. When the first and second screw rods 2 and 3 approach each other, the rod having a smaller diameter can extend into the tube having a larger diameter, increasing the relative telescopic displacement between the first and second screw rods 2 and 3.

Figure 6:
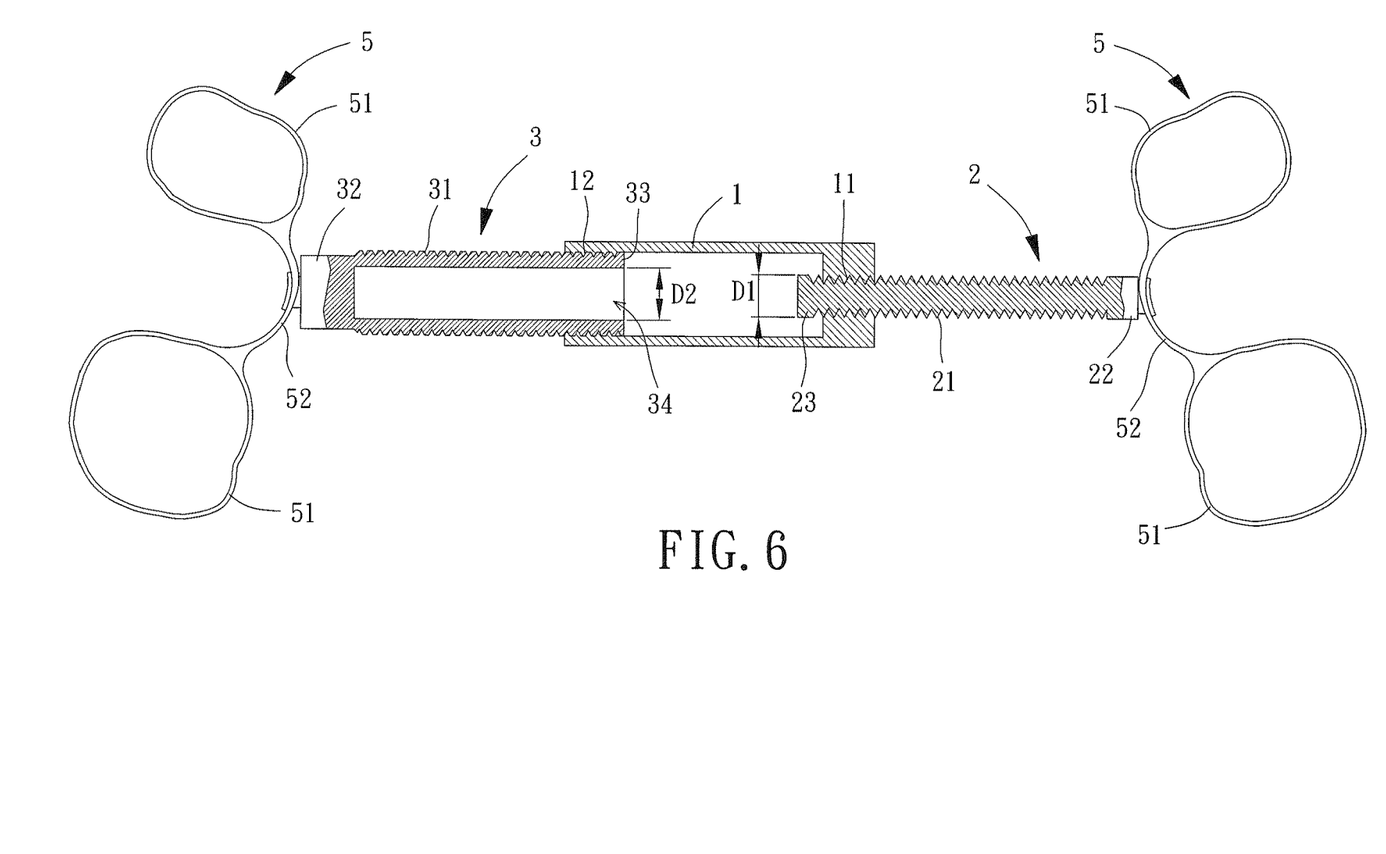
FIG. 6 is a cross sectional view of the orthodontic remodeling device of FIG. 5 after assembly.

With reference to FIG. 6, in a case that the first screw rod 2 is a rod having a smaller diameter and the second screw rod 3 is a tube having a larger diameter, the first screw rod 2 has a maximum diameter D1 at the first threaded portion 21 and the first stopper portion 23 (or from the first axial end through the second axial end) of the first screw rod 2. Furthermore, the second screw rod 3 includes a receiving hole 34 having an opening in the second stopper portion 33 at the second axial end of the second screw rod 3. The receiving hole 34 has a minimum diameter D2 larger than the maximum diameter D1 of the first screw rod 2.

Thus, when the sleeve 1 is rotated to control the first and second screw rods 2 and 3 to synchronously move toward each other, movement of the first and second screw rods 2 and 3 will not stop even though the first stopper portion 23 of the first screw rod 2 and the second stopper portion 33 of the second screw rod 3 pass through the same radial plane. Instead, the sleeve 1 can be further rotated, such that the first threaded portion 21 and the first stopper portion 23 of the first screw rod 2 extend into the receiving hole 34 of the second screw rod 3 (see FIG. 7). Thus, the relative displacement of the first and second screw rods 2 and 3 toward or away from each other can be increased, which can be applicable to patients of various mouth sizes.

With reference to FIGS. 5 and 6, each of the first and second screw rods 2 and 3 can be assembled with a tooth pushing member 5 capable of pushing two or more to-be-pushed-outward teeth T at the same time. Specifically, each tooth pushing member 5 includes a plurality of tooth coupling rings 51 to be mounted around a plurality of teeth T on the same side of the upper jaw of the patient. Two adjacent tooth coupling rings 51 are connected by a connecting plate 52. Thus, the first assembling portion 22 is rotatably connected to one of the connecting plate 52 and the tooth coupling rings 51 of one of the two tooth pushing members 5. The second assembling portion 32 is rotatably connected to one of the connecting plate 52 and the tooth coupling rings 51 of the other tooth pushing member 5. Preferably, the one of the connecting plate 52 and the tooth coupling rings 51, which is rotatably connected to the first assembling portion 22, is located at a middle portion of one of the two tooth pushing members 5. Preferably, the one of the connecting plate 52 and the tooth coupling rings 51, which is rotatably connected to the second assembling portion 32, is located at a middle portion of the other of the two tooth pushing members 5.

Figure 7:
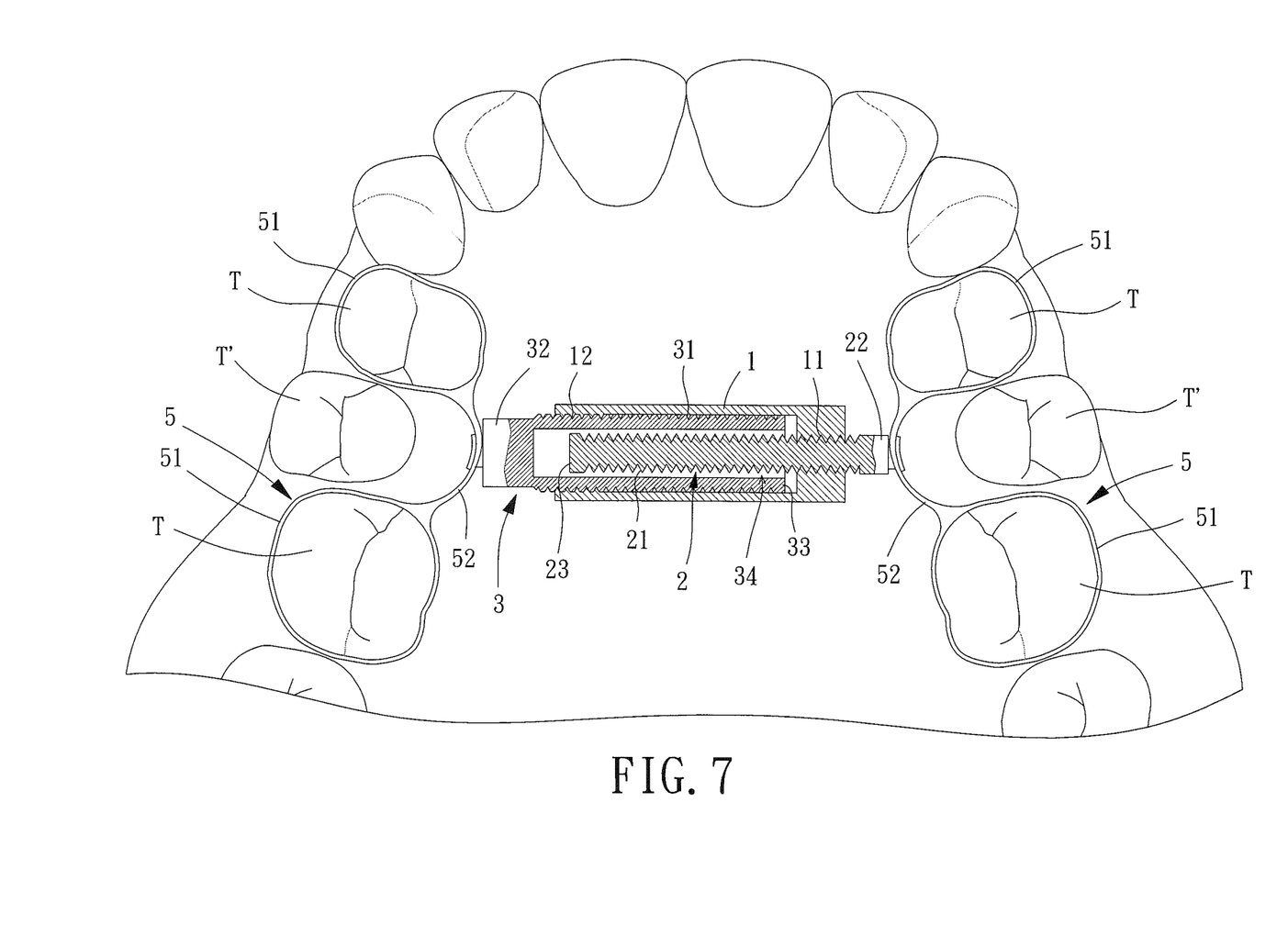
FIG. 7 is a diagrammatic view illustrating use of the orthodontic remodeling device of FIG. 6 in a mouth of a patient.

In the non-restrictive embodiment shown in FIGS. 5-7, each tooth pushing member 5 includes two tooth coupling rings 51 and a connecting plate 52. The size of the connecting plate 52 is decided by the spacing required between the two tooth coupling rings 51. For example, the two tooth coupling rings 51 of each tooth pushing member 5 are mounted around two to-be-pushed-outward teeth T between which an intermediate tooth T' is located. In this case, the length of the connecting plate 52 is slightly larger than the width of the intermediate tooth T'. In another case that the two to-be-pushed-outward teeth T are contiguous to each other, the length of the connecting plate 52 is shorter. Likewise, the length of the connecting plate 52 is larger when the spacing between the two to-be-pushed-outward teeth T is larger. The profiles of the tooth pushing members 5 can be adjusted according to needs, which can be appreciated by one having ordinary skill in the art.

With reference to FIG. 7, in use of the orthodontic remodeling device of this embodiment, the operator places the orthodontic remodeling device into the mouth of a patient and rotates the sleeve 1 to adjust the two tooth pushing members 5 to have a proper spacing therebetween. Then, the plurality of tooth coupling rings 51 of the two tooth pushing members 5 are mounted around a plurality of to-be-pushed-outward teeth T on two sides of the upper jaw of the patient, rapidly completing mounting of the orthodontic remodeling device. After mounting, the operator slightly rotates the sleeve 1 to slightly and synchronously move the first and second screw rods 2 and 3 away from each other, such that the two tooth pushing members 5 exert outward pushing forces on the to-be-pushed-outward teeth T coupled with the two tooth pushing members 5. After a period of time, the to-be-pushed-outward teeth T can be pushed back to the normal dentition line.

Since the patient has two to-be-pushed-outward teeth T on each side of the upper jaw of the patient and since the intermediate tooth T' between the two to-be-pushed-outward teeth T is located in the normal tooth line, the two tooth coupling rings 41 of each tooth pushing member 4 are respectively mounted around the two to-be-pushed-outward teeth T, and the corresponding connecting plate 52 is aligned with the intermediate teeth T', the connecting plate 52 will not come into contact with the intermediate tooth T' while the two to-be-pushed-outward teeth T are pushed outward by a corresponding tooth pushing member 5. Thus, the intermediate tooth T' is not affected.

Note that the first and second screw rods 2 and 3 of the first embodiment can be assembled with the tooth pushing members 5 of the second embodiment, and the first and second screw rods 2 and 3 of the second embodiment can be assembled with the tooth pushing members 4 of the first embodiment. In a case that the patient has only one to-be-pushed-outward tooth on the upper jaw, the to-be-pushed-outward tooth and another tooth opposite to the to-be-pushed-outward tooth are pushed outward synchronously. After the to-be-pushed-outward tooth is pushed back to the normal dentition line, arch wires can be used to apply forces to correct and position the corresponding teeth. The orthodontic remodeling device according to the present invention can be used to correct irregular teeth on the lower jaw of a patient.

In view of the foregoing, the orthodontic remodeling device according to the present invention can be easily and rapidly mounted in the mouth of the patient without causing wounds to thereby reduce the risk of infection. The orthodontic remodeling device can be pushed outward from the inner side of the teeth, such that the indented teeth can be gradually pushed back to the normal dentition line. Then, arch wires can be used to apply forces for correcting and positioning the teeth, achieving an excellent effect of correcting the irregular teeth while significantly reducing the time for correction and increasing the correction efficiency.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. An orthodontic remodeling device comprising:
   a sleeve including a first screw hole in an end thereof and a second screw hole in another end thereof, with the first screw hole having a thread direction opposite to a thread direction of the second screw hole;
   a first screw rod including a first threaded portion and a first assembling portion, with the first threaded portion threadedly engaged with the first screw hole, and with the first assembling portion exposed outside of the sleeve;
   a second screw rod including a second threaded portion and a second assembling portion, with the second threaded portion threadedly engaged with the second screw hole, and with the second assembling portion exposed outside of the sleeve; and
   two tooth pushing members respectively engaged with the first and second assembling portions, with each of the two tooth pushing members including at least one tooth coupling ring adapted to be mounted on at least one tooth of a patient and adapted to push the at least one tooth outward,
   wherein the sleeve is rotatable to move the first and second screw rods toward or away from each other to change a relative position between the two tooth pushing members,
   with the first screw rod having first and second axial ends, with the first assembling portion disposed at the first axial end of the first screw rod, with the first screw rod further including a first stopper portion on the second axial end thereof, with the first stopper portion having a planar end face, with the first threaded portion located between the first assembling portion and the first stopper portion, with the second screw rod having first and second axial ends, with the second assembling portion disposed on the first axial end of the second screw rod, with the second screw rod further including a second stopper portion on the second axial end of the second screw rod, with the second stopper portion having a planar end face, with the second threaded portion located between the second assembling portion and the second stopper portion, wherein the sleeve is rotatable to move the first and second screw rods toward each other until the first and second stopper portions of the first and second screw rods abut each other to prevent further rotation of the sleeve,
   with the at least one tooth coupling ring of one of the two tooth pushing members including a tooth coupling ring rotatably connected to the first assembling portion, and with the at least one tooth coupling ring of another of the two tooth pushing members including a tooth coupling ring rotatably connected to the second assembling portion.

2. The orthodontic remodeling device as claimed in claim 1, wherein the first screw hole has a central axis coincident to a central axis of the second screw hole.

3. The orthodontic remodeling device as claimed in claim 1, wherein the first screw hole and the second screw hole have an identical pitch.

4. The orthodontic remodeling device as claimed in claim 1, wherein the at least one tooth coupling ring of each of the two tooth pushing members is a closed, annular ring having an inner periphery corresponding to a contour of the at least one tooth.

5. The orthodontic remodeling device as claimed in claim 1, with the at least one tooth coupling ring of each of the two tooth pushing members including a plurality of tooth coupling rings, with two adjacent tooth coupling rings connected by a connecting plate, with the first assembling portion rotatably connected to one of the connecting plate and the plurality of tooth coupling rings of one of the two tooth pushing members, and with the second assembling portion rotatably connected to one of the connecting plate and the plurality of tooth coupling rings of another of the two tooth pushing members.

6. The orthodontic remodeling device as claimed in claim 5, wherein the one of the connecting plate and the plurality of tooth coupling rings, which is rotatably connected to the first assembling portion, is located at a middle portion of the one of the two tooth pushing members, and wherein the one of the connecting plate and the plurality of tooth coupling rings, which is rotatably connected to the second assembling portion, is located at a middle portion of the other of the two tooth pushing members.

7. The orthodontic remodeling device as claimed in claim 1, wherein the first and second screw rods have an identical configuration except the thread directions.

\* \* \* \* \*